US00PP30631P3

(12) United States Plant Patent
Plocher

(10) Patent No.: US PP30,631 P3
(45) Date of Patent: Jul. 2, 2019

(54) GRAPE PLANT NAMED 'VERONA'

(50) Latin Name: ***Vitis* interspecific hybrid**
Varietal Denomination: Verona

(71) Applicant: Thomas Alan Plocher, Hugo, MN (US)

(72) Inventor: Thomas Alan Plocher, Hugo, MN (US)

( * ) Notice: Subject to any disclaimer, the term of this patent is extended or adjusted under 35 U.S.C. 154(b) by 0 days.

(21) Appl. No.: 15/530,152

(22) Filed: Dec. 6, 2016

(65) Prior Publication Data

US 2018/0160589 P1 Jun. 7, 2018

(51) Int. Cl.
*A01H 5/08* (2018.01)
*A01H 6/88* (2018.01)

(52) U.S. Cl.
USPC ..... Plt./205
CPC ..... *A01H 5/08* (2013.01); *A01H 6/88* (2018.05)

(58) Field of Classification Search
USPC ..... Plt./205
CPC ..... A01H 5/0812
See application file for complete search history.

(56) References Cited

PUBLICATIONS https://www.winesandvines.com/news/article/158849/New-Cold-Climate-Grapes-Named; Oct. 6, 2015; 8 pages.*

* cited by examiner

*Primary Examiner* — Kent L Bell
(74) *Attorney, Agent, or Firm* — Michelle Bos Legal LLC

(57) ABSTRACT

'Verona' is a late-budding grape variety notable for its cold hardiness, large cluster size and suitability as a red wine grape.

7 Drawing Sheets

Latin name: *Vitis* interspecific hybrid.
Variety denomination: 'Verona'.

BACKGROUND OF THE VARIETY

'Verona' is a new and distinct variety of grape plant selected from a group of seedlings resulting from a controlled cross of female parent 'Troubador' (not patented) and male parent 'E.S. 5-4-16' (not patented) carried out at Hugo, Minn. in 1997. 'Verona' was selected for its excellent winter hardiness, late bud break in springtime, large cluster size and excellent suitability as a red wine grape. Asexual propagation by hardwood cutting was first carried out in 2004 at Hugo, Minn.; subsequent asexual propagations have shown the variety to be stable and to reproduce true to type through successive generations.

BRIEF DESCRIPTION OF THE VARIETY

'Verona' is a late-budding grape variety notable for its cold hardiness, large cluster size and suitability as a red wine grape. Red wine produced from 'Verona' grapes exhibits good balance, moderate acidity, abundant tannins, and complex aromas of raspberry with a hint of chocolate.

A comparison of 'Verona' to its parents is shown in Table 1 below.

TABLE 1

Comparison of 'Verona' to Parent Varieties

| | 'Verona' | 'Troubador' | 'ES 5-4-16' |
|---|---|---|---|
| Winter hardiness | −32 to −35° C. | −40° C. | −32 to −35° C. |

TABLE 1-continued

Comparison of 'Verona' to Parent Varieties

| | 'Verona' | 'Troubador' | 'ES 5-4-16' |
|---|---|---|---|
| Bud break | 100% first swell stage at 112 DDF 50 | Much earlier, similar to Marquette | Similar to Verona |
| Acidity at harvest | 0.8% | 1.4% | 0.8% |
| pH | 3.38 | Much lower than 'Verona' | Similar to 'Verona' |
| Berry size | Larger, 14.78 mm avg. diameter | 7-8 mm | 15-17 mm |
| Cluster size | 145 g | 45 g | 200 g |

A comparison of 'Verona' to 'Marquette' (U.S. Plant Pat. No. 19,579), another cold-hardy variety, is shown in Table 2 below.

TABLE 2

Comparison of 'Verona' to Similar Variety

| | 'Verona' | 'Marquette' |
|---|---|---|
| Winter hardiness | Very hardy | Hardy |
| Bud break | Late April, about 12 days after 'Marquette' | Mid-April |
| Acidity at harvest | Lower - 0.8% | Higher - 1.1% to 1.2% |
| Vigor | Less vigorous | More vigorous |
| Skin tannins | Higher concentration, extractible | Lower concentration, not extractible |

BRIEF DESCRIPTION OF THE PHOTOGRAPHS

The photographs show selected characteristics of an eight-year-old 'Verona' grape plant grown on its own roots, taken during the 2016 growing season at Hugo, Minn.

DETAILED BOTANICAL DESCRIPTION OF THE VARIETY

Figure 1:
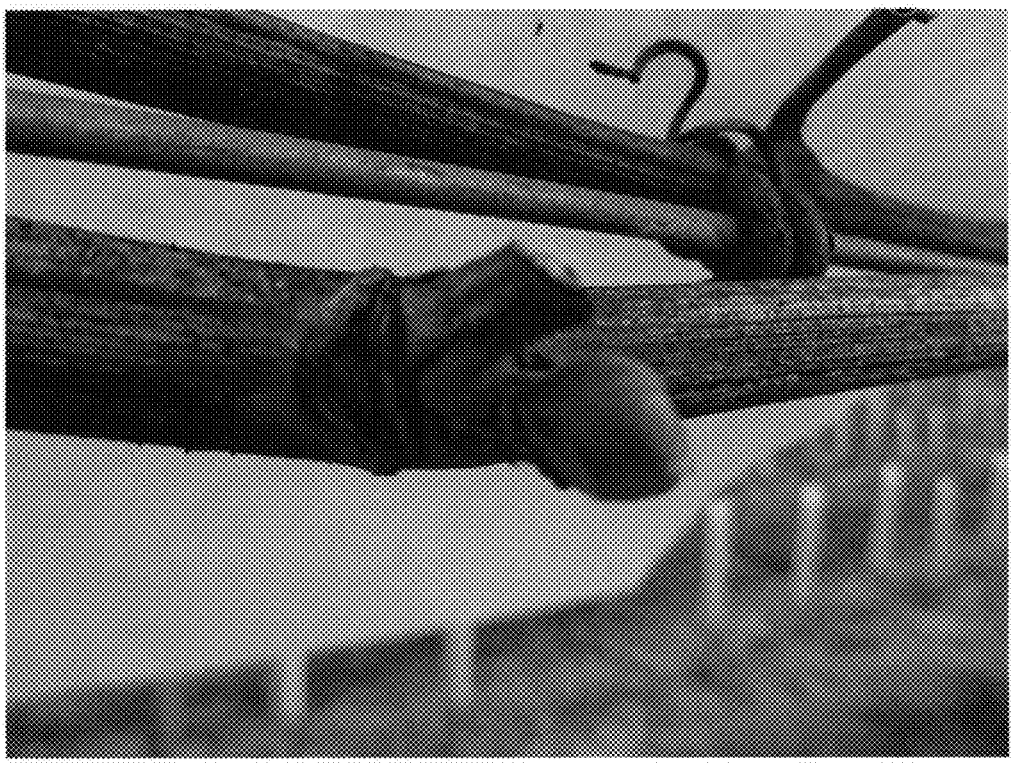
FIG. 1 shows a bud at first swell stage.
Figure 2:
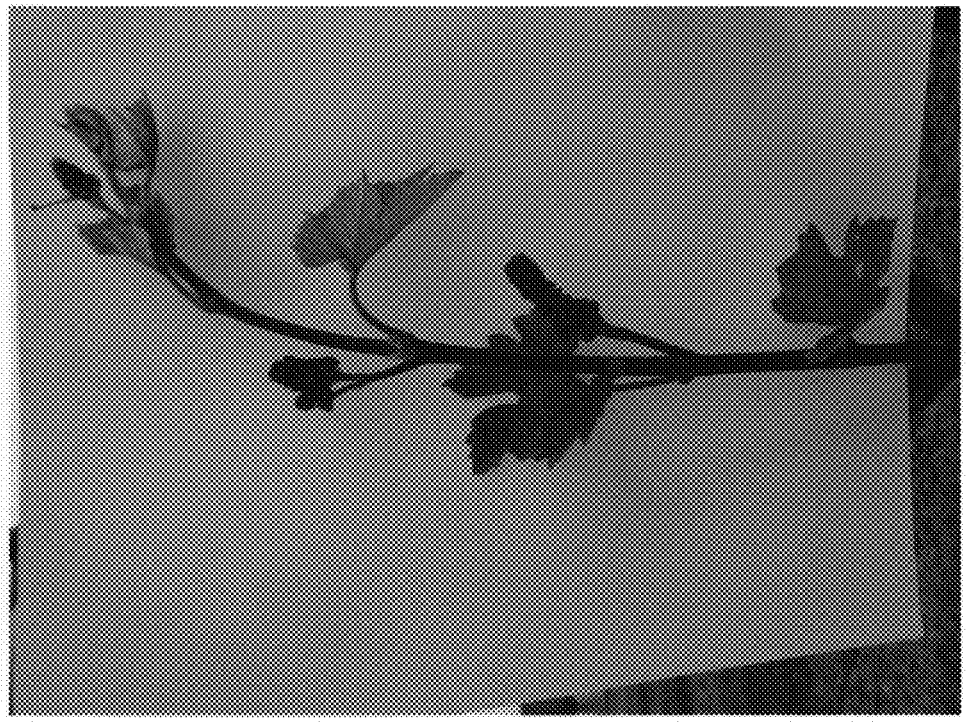
FIG. 2 shows a young shoot and leaves.
Figure 3:
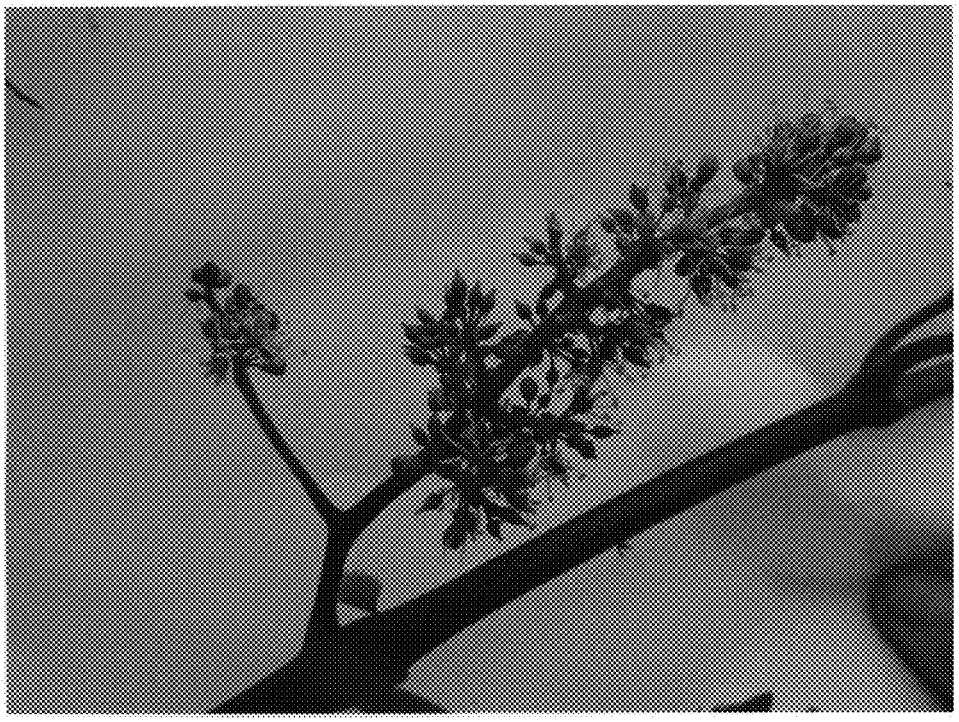
FIG. 3 shows an inflorescence.
Figure 4:
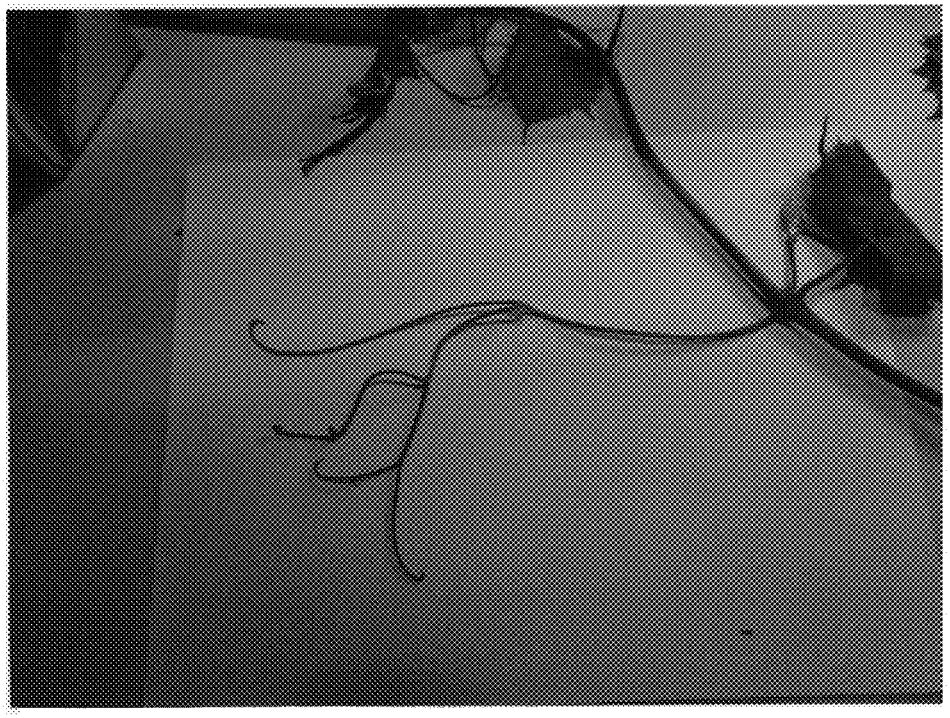
FIG. 4 shows leaves and tendrils.
Figure 5:
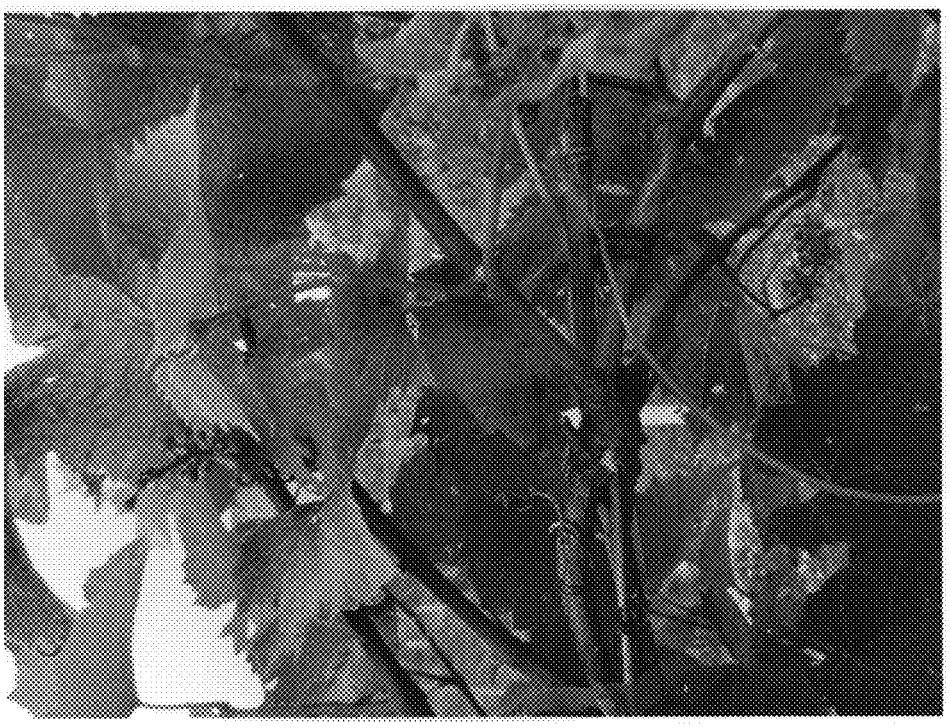
FIG. 5 shows the vine, leaves, young shoots and inflorescences.
Figure 6:
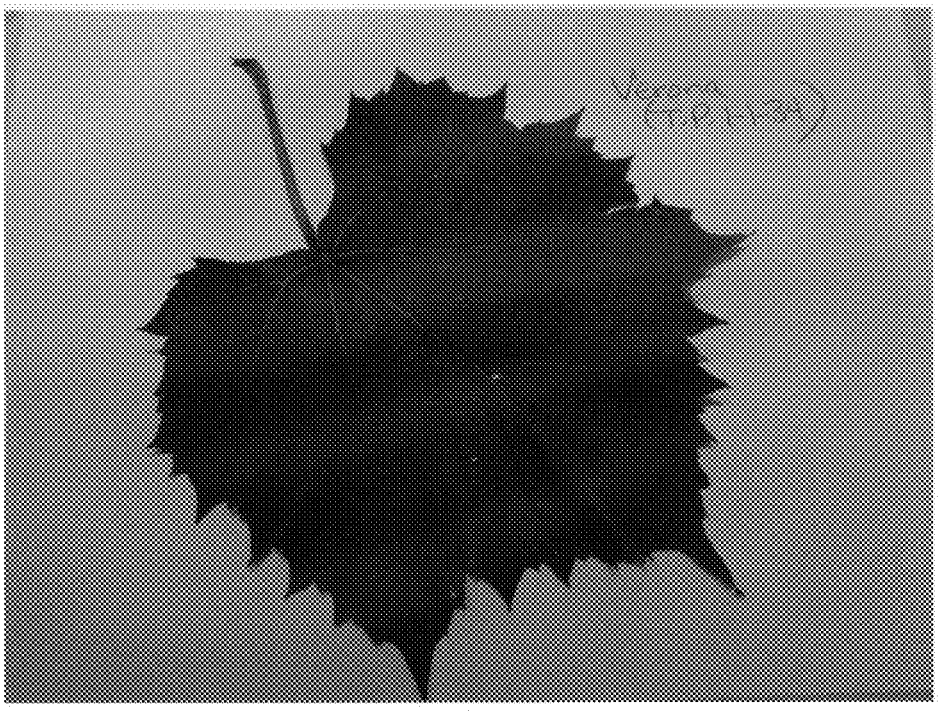
FIG. 6 shows a leaf.
Figure 7:
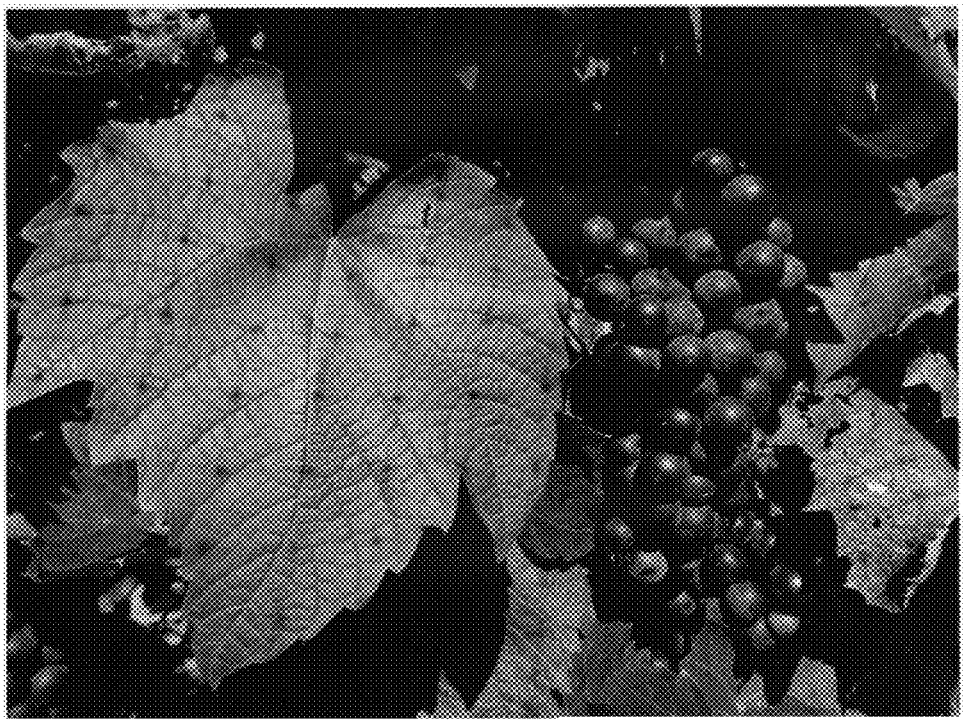
FIG. 7 shows a typical cluster and leaf.

The following-detailed botanical description is based on observations made during the 2016 growing season at Hugo, Minn. of eight-year-old vines growing on their own roots. All colors are described according to The Royal Horticultural Society Colour Chart (Sixth edition). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. "DDF 50" means "Degree Days Fahrenheit Base 50" and refers to accumulated heat units.

Vine:

*Size.*—Medium to large.

*Form.*—Semi-procumbent.

*Vigor.*—Moderate to high, depending on soil.

*Timing of bud burst.*—30 Apr. 2016 (100% first swell stage at 112 DDF 50); approximately 12 days later than 'Marquette'.

*Productivity.*—3 to 6 tons per acre.

*Trunk diameter.*—2.0 cm at 76 cm above the ground on 3 year old trunks.

*Bark texture.*—Moderately rough.

*Bark color.*—Brown N200B.

Canes:

*Diameter.*—7.6 mm (measured immediately distal to $4^{th}$ node).

*Quantity.*—Typical pruning to 30 buds giving rise to 30 canes.

*Bark color.*—Grey-brown 200D.

*Bark texture.*—Smooth with moderate longitudinal lines.

*Form.*—Slightly flattened in cross section.

*Node size.*—13.4 mm (measured at $4^{th}$ node).

*Internode length.*—11 cm (measured between $3^{rd}$ and $4^{th}$ full node).

*Number of tendrils per node.*—Pattern is two consecutive nodes, each with a single tendril, followed by one or two consecutive nodes with no tendrils.

*Tendril thickness.*—1.5 to 2.0 mm, average 1.625 mm.

*Tendril length.*—Natural (uncurled) 13 cm; stretched 16 cm.

*Tendril texture.*—Smooth.

*Young tendril color.*—Strong yellow green 144B.

Flowers:

*Fertility.*—Self-fertile.

*Date of bloom.*—10 Jun. 2016 (approximately 435 DDF 50 from 100% first swell to 50% caps off).

*Number of inflorescences per shoot.*—2.

*Numbers of flowers per inflorescence.*—450.

*Shape of flower cluster.*—Conical with small wing; cluster has characteristic curvature that appears just distal to the wing and is described by an arctangent of 0.14 to 0.25, subtending an angle of 8 to 14 degrees.

*Length of flower cluster.*—10 cm.

*Width of flower cluster.*—Ranges from 3.8 cm at the fullest extent of the wing to 1.7 cm for the main flower cluster.

*Filament length.*—4 mm.

*Filament color.*—White N155D.

*Anther length.*—0.8 to 1 mm.

*Anther color.*—Yellow 11B.

*Pistil length.*—2.5 to 3.0 mm.

*Pistil diameter.*—1.3 mm.

*Pistil color.*—Green 141D; Many pistils splashed with orange-red N34A to orange-red N34B around the stigma and down the sides of the pistil to varying degrees.

*Pedicel length.*—3.5 to 4.0 mm.

*Pedicel diameter.*—0.20 to 0.25 mm.

*Pedicel color.*—Green 141D with orange-red N34A to orange-red N34B where stem meets pistil.

*Flower type.*—Hermaphroditic.

*Stamen color.*—White N155D.

*Stamen length.*—4 mm.

*Stamen quantity.*—4 to 6.

*Cap color.*—Yellow-green 144C with a splash of orange-red N34A to orange-red N34B in the center of the cap.

Young shoots (measured at flowering):

*Openness of the tip.*—Almost completely closed.

*Density of prostrate hairs on tip.*—Very dense.

*Anthocyanin coloration of prostrate hairs on tip.*—Pronounced deep red-purple 70C on medial portion of shoot tip along central vein.

Young leaf ($4^{th}$ distal leaf at flowering):

*Shape.*—Circular.

*Length.*—11.7 cm to 15.5 cm, average 13.1 cm.

*Width.*—10.0 to 14.0 cm, average 11.8 cm.

*Color of upper side of the blade.*—Green 144A.

*Color of lower side of the blade.*—Moderate yellow green 139C.

*Density of prostrate hairs between main veins on lower side of blade.*—Strong.

*Density of erect hairs on main veins on lower side of blade.*—Strong, especially along both sides of the vein.

Mature leaves (measured just before veraison):

*Relative size.*—Medium.

*Length.*—12 to 18.5 cm, average 15.5 cm.

*Width.*—11 to 18.5 cm, average 15.1 cm.

*Thickness.*—0.019 mm to 0.023 mm, average 0.021 mm.

*Shape.*—Circular.

*Margin.*—Erose.

*Base.*—Cordate.

*Color.*—Upper surface — Green 138A.

*Color.*—Lower surface — Green 138B.

*Texture*.—Upper surface — Nearly hairless between veins save for an occasional erect hair; moderately corrugated; rather dense prostrate hairs on veins.
*Texture*.—Lower surface — Hairless between veins; rather dense prostrate hairs on veins.
*Number of lobes*.—3.
*Terminal lobe*.—Form — Pointed.
*Petiole color*.—Red-purple 59B, with yellow-green 144B striping.
*Petiole sinus depth*.—2.0 to 3.6 cm, average 2.8 cm.
*Petiolar sinus shape*.—V-shaped to U-shaped.
*Petiolar sinus*.—Relative arrangement of lobes — Wide open.
*Petiole sinus limited by veins?*.—Yes.
*Anthocyanin coloration of main veins on upper side of blade*.—None.
*Petiole length*.—6.2 to 10.8 cm, average 8.39 cm.
*Petiole diameter*.—2.8 mm to 3.9 mm, average 3.3 mm.
*Density of prostrate hairs between main veins on lower side of blade*.—Sparse.
*Density of erect hairs on main veins on lower side of blade*.—Medium-high.
*Length of middle vein*.—9.7 to 15 cm, average 13.3 cm.
*Petiole length/length of middle vein*.—0.55 to 0.76, average 0.66.
*Lateral sinus depth*.—Left side — 1.0 to 2.5 cm, average 1.68 cm.
*Lateral sinus depth*.—Right side — 1.3 to 2.5 cm, average 1.81 cm.
*Lateral sinus shape*.—Shallow U-shape or V-shape; often asymmetrical.
Relative arrangement of lateral sinus lobes.—Wide open.
*Length of teeth*.—0.6 to 1.4 cm, average 0.98 cm.
*Width of teeth*.—0.8 to 1.7 cm, average 1.2 cm.
*Ratio of length/width of teeth*.—0.7 to 0.91, average 0.81.

Mature tendrils (measured after veraison, August 27):
*Quantity*.—Pattern is two consecutive nodes, each with a single tendril, followed by one or two consecutive nodes with no tendrils.
*Thickness*.—1.5 to 2.0 mm, average 1.625 mm.
*Length*.—Natural (uncurled) 13 cm; stretched 16 cm.
*Form*.—Branched with at least one branch of the main tendril.
*Tendril color*.—Strong yellow green 144C; occasional strong purplish red 64B overlaid on the green on the lower half of the tendril.
*Texture*.—Smooth.

Shoot (measured at flowering):
*Attitude* (*before tying*).—45-60 degrees measured at the base of the shoot between the shoot and the cane from which it grew.
*Color of dorsal side of internode* (*well illuminated*).—Yellow-green 144A with red-purple 59A stripes.
*Color of ventral side of internode* (*without direct sunlight*).—Yellow-green 144A.
*Density of erect hairs on internodes*.—Present but very sparse.
*Number of consecutive tendrils*.—Discontinuous; pattern is two consecutive nodes, each with a single tendril, followed by one node with no tendril.
*Length of tendrils*.—23 to 26 cm, stretched out.
*Thickness of tendril*.—2 mm (measured just proximal to the branching).
*Form of tendril*.—With two points of branching, one halfway up the tendril and the other at the end of one of the first branches.
*Hairs on internodes*.—Erect hairs present, but sparse.
*Color of tendril*.—Yellow-green 144A with red-purple 59A speckle.

Fruit:
*Maturity date*.—168 days after bud break, or 2607DDF 50, in Hugo, Minn. (45.1600° N, 92.9933° W); Relative timing is late season, early to mid October.
*Shape*.—Round and slightly flattened (width slightly exceeds length).
*Length*.—12 mm to 18 mm, average 14 mm.
*Width*.—8 mm to 10.5 mm, average 10 mm.
*Relative size*.—Larger than 'Petite Pearl' (not patented) and 'Crimson Pearl' (U.S. Plant patent application Ser. No. 15/530,160).
*Brix*.—19 to 22 degrees.
*Skin thickness*.—0.48 to 0.72 mm, average 0.60 mm.
*Skin color*.—Blue 103A overlaid with some violet-blue 98A.
*Tendency to crack*.—No tendency to crack, even under wet conditions.
*Flesh color*.—Green-white 157A.
*Flesh texture*.—Slipskin.
*Juice color*.—Deep Red 53A.
*Juice production*.—18 lbs. (8.16 kg) fruit produces 1 gallon (3.78 L) finished wine.
*Anthocyanin coloration*.—On skin and streaked around seeds, Strong Purplish Red 61B.
*Flavor*.—Pronounced raspberry flavor.
*Aroma*.—Slightly raspberry; more pronounced in wine made from 'Verona' grapes.
*Seed length*.—4.83 to 5.82 mm, average 5.4 mm.
*Seed width*.—3.30 to 4.75 mm, average 3.9 mm.
*Seed thickness*.—2.83 to 3.43 mm, average 3.1 mm.
*Seed shape*.—Pyriform.
*Seed color*.—Grey-brown N199C.

Cluster:
*Overall shape*.—Cylindrical with a distinct wing and a characteristic bend to the cluster; tightly packed with berries.
*Relative size*.—Larger than 'Petite Pearl' or 'Crimson Pearl'.
*Weight*.—92 to 180 g, average 145 g.
*Number of berries per cluster*.—57 to 96, average 76 berries per cluster.
*Length*.—12 to 18 cm, average 15.1 cm.
*Width*.—8 to 10.5, average 9.4 cm.
*Peduncle length*.—4.72 to 8.54 mm, average 6.35 mm.
*Peduncle thickness*.—1.72 to 2.32 mm, average 2.05 mm.
*Peduncle color*.—Strong yellow green 143B.
*Pedicel length*.—11 to 18 mm, average 15.7 mm.
*Pedicel thickness*.—3.93 to 5.57 mm, average 4.79 mm.
*Market use*.—Production of red and rose wine.
*Disease resistance/susceptibility*.—Good resistance to downy mildew (*Plasmopara viticola*) and powdery mildew (*Erysiphe necator* (Schw.) Burr.); Good resistance to black rot (*Guignardia bidwellii*).

I claim:

1. A new and distinct grape plant substantially as described and illustrated herein.

* * * * *